United States Patent [19]
Andrese

[11] Patent Number: 5,176,128
[45] Date of Patent: Jan. 5, 1993

[54] ORGAN RETRACTOR

[76] Inventor: Craig A. Andrese, 128 Stirrup La., Burr Ridge, Ill. 60521

[21] Appl. No.: 645,129

[22] Filed: Jan. 24, 1991

[51] Int. Cl.⁵ .............................................. A61B 17/02
[52] U.S. Cl. ....................................................... 128/20
[58] Field of Search ................... 128/20; 606/198, 200; 604/104

[56] References Cited
U.S. PATENT DOCUMENTS

| 4,190,042 | 2/1980 | Sinnreich | 128/20 |
| 4,654,028 | 3/1987 | Suma | 604/106 |
| 4,727,873 | 3/1988 | Mobin-Uddin | 606/200 |
| 4,784,150 | 11/1988 | Voorhies et al. | 128/664 |
| 4,969,891 | 11/1990 | Gewertz | 606/200 |
| 4,997,435 | 3/1991 | Demeter | 606/127 |

FOREIGN PATENT DOCUMENTS 2580504 10/1986 France ............................. 606/200

Primary Examiner—Robert P. Swiatek
Assistant Examiner—Cindy A. Cherichetti
Attorney, Agent, or Firm—Edmond T. Patnaude

[57] ABSTRACT

An organ retractor includes a tubular introducer which is adapted to be inserted through a body into an underlying body cavity and a multi-fingered tool which is insertable into through the body wall into the body cavity. The fingers are formed of a spring material and have a naturally curved configuration so as to spread out when pushed beyond the distal end of the introducer. A plurality of filaments attached to the fingers provide bridges when the fingers are in the extended positions.

10 Claims, 2 Drawing Sheets

ORGAN RETRACTOR

The present invention relates in general to surgical instruments, and it relates in particular to a new and improved surgical instrument for holding one or more organs or other internal parts of a human body away from the area of an organ being operated on during laparoscopic surgery.

BACKGROUND OF THE INVENTION

Laparoscopic surgery is performed by the insertion of one or more instruments into a body cavity through very small incisions in the skin of the patient. Unlike ordinary surgery where the part of the body being operated on is exposed to the atmosphere, in laparoscopic surgery the body cavity remains closed from the atmosphere whereby the organs tend to remain in their normal positions, i.e. they are in intimate contact with one another in a relatively soft mass. In order to facilitate access to the area of an organ being worked on, pressurized gas is introduced into the body cavity to move and hold the skin, muscle and fatty tissues away from the area at which surgery is to be performed. However, because of the physical nature of the internal organs, they move under the force of gravity into intimate contact with one another making it difficult for the surgeon to see the area being worked on and to perform surgery on the selected one of the organs without damage to other ones of the nearby organs.

SUMMARY OF THE INVENTION

Briefly, there is provided in accordance with the present invention a new and improved surgical instrument for retracting and holding internal organs away from the surgical area in a body cavity of a human being or other animal being operated on during laparoscopic surgery. The instrument includes a tubular introducer which is adapted to extend through the skin of the patient into the body cavity and through which an organ retractor tool may be introduced into the body cavity.

The retractor tool includes a plurality of elongate spring fingers, the end portions of which spread apart as the fingers are pushed out of the end of the introducer. The fingers are non-circular in cross-section and are angularly adjustable to control the direction in which the respective fingers diverge from the axis of the introducer as they are pushed through the open end of the introducer. The retractor tool further includes a rigid, centrally disposed post having longitudinal passageways therethrough opening onto the sides of the post facing the respective fingers. A plurality of bridging and retraction filaments extend through the passageways and are respectively secured at the distal ends to the respective fingers. Consequently, the fingers in combination with the central post and the bridging sections of the filaments provide a mesh-like member having sufficient strength and rigidity to push and hold an internal body organ away from the area to be worked on. Upon conclusion of the surgery the filaments are retracted through the central post to pull the extended portions of the fingers into parallel relationship with the post and thus facilitate withdrawal of the tool from the body cavity through the introducer tube.

A clamp member is provided to secure the fingers in both the angularly and longitudinally adjusted positions and to maintain the filaments in a taut condition during use of the tool.

GENERAL DESCRIPTION OF THE DRAWINGS

A better understanding of the present invention may be had from a reading of the following detailed description taken in connection with the accompanying drawings wherein.

DETAILED DESCRIPTION OF A PREFERRED EMBODIMENT

Figure 1:
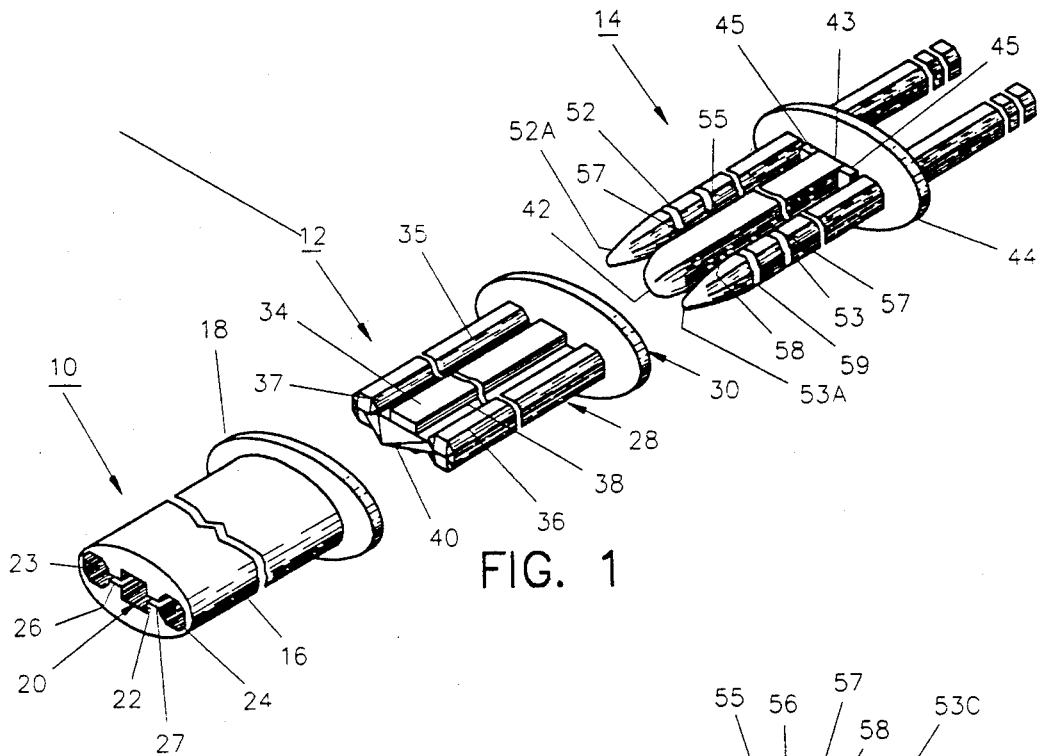
FIG. 1 is an exploded isometric view of a surgical instrument embodying the present invention.

Referring particularly to FIG. 1, there is shown an introducer 10, which is adapted to be inserted through the skin, muscle and fatty tissues into a body cavity, an incision tool 12, which is used in conjunction with the introducer to make an incision through which the introducer is inserted the body cavity, and an organ retractor tool 14, which is subsequently inserted through the introducer into the body cavity for use in moving and holding internal parts of the body away from the area being operated on. In use, the incision tool is first inserted into the introducer by inserting it into the longitudinal passageway through the introducer, and after an incision has been made in the skin the assembly is pressed against the underlying tissues to simultaneously cut a short slit therein and push the introducer therethrough until the introducer is fully inserted and the distal end thereof is within the body cavity.

The introducer 10 may be seen to include an elongate body section 16 having an external flange 18 at one end thereof. A passageway 20 extends longitudinally through the body section and the flange from one end of the introducer to the other. The passageway 20 includes a central section 22 which is generally square in cross section, a pair of polygonal sections 23 and 24, and a pair of narrow sections 26 and 27 which respectively connect the sections 23 and 24 to the central section 22.

The incision tool 12 may be seen to include a solid, elongate body section 28 and an external flange section 30 at one end of the body section. The flange 30 has the same external size and shape as the flange 18, but this is not critical. The body section 28 is complementary in cross section to the passageway 20 in the introducer 10 and is also of approximately the same length. The body section 28 thus has a square central section 34, a first polygonal section 35, a second polygonal section 36 and generally rectangular sections 37 and 38 which connect the sections 35 and 36 to the central section 34. A triangular knife blade 40 extends from the end of the body 28 a short distance beyond the distal end of the introducer when the incision tool is fully inserted into the introducer which the flanges 18 and 30 in mutual abutment. The polygonal sections 35 and 36 are octagonal in cross section and the respective sides thereof taper inwardly toward the points at which the respective ends of the blade are positioned. The tapered end portions extend beyond the distal end of the introducer when the incision tool 12 is fully inserted into the introducer 10.

The organ retractor tool 14 may be seen to include an elongate central post to one end 43 of which a flange member 44 is affixed. The flange 44 preferably has the same size and shape as the flanges 18 and 30, and the post 42 is centrally located with respect to the flange 44. A pair of sealing gaskets 45 are positioned on opposite sides of the post 43 for sealing engagement with the outer face of the flange 18 on the introducer to prevent leakage of gas from the body cavity through the passageways 26 and 27.

Figure 2:
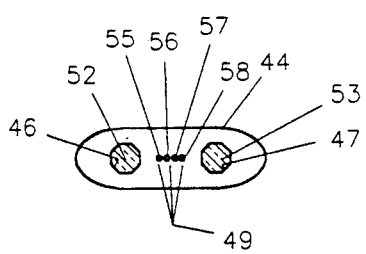
FIG. 2 is an elevational view of the instrument of FIG. 1 during use thereof, the retractor tool being shown in the operative position.

As best shown in FIG. 2, the flange 44 has a pair of octagonal through holes 46 and 47 and a plurality of circular holes 49. The holes 46 and 47 are identical in cross section to the holes 23 and 24 in the introducer 10 and each slidably receives one of a pair of spring fingers 52 and 53 which are complementary in cross section to the openings 23, 24, 46, and 47 and are slidably received therein. The distal ends 52A and 53A of the fingers 52 and 53 are rounded to prevent damage to the internal parts of the body during use of the instrument.

Figure 3:
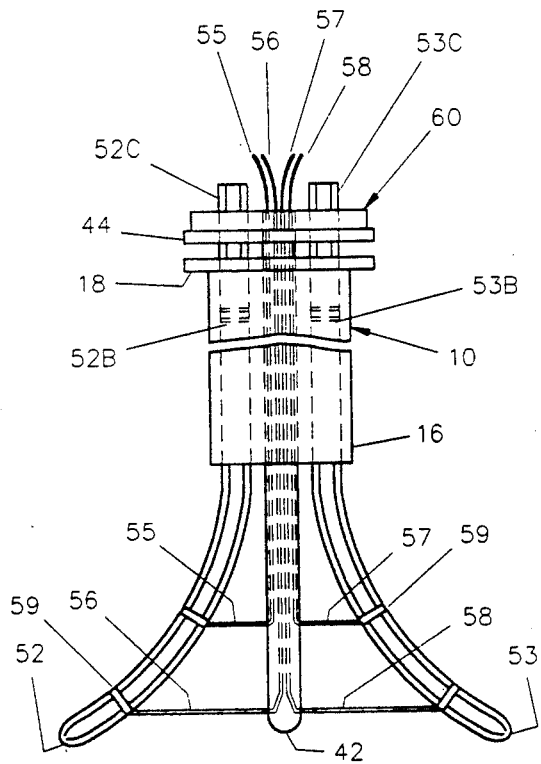
FIG. 3 is a top view of the instrument as it is shown in FIG. 2.
Figure 4:
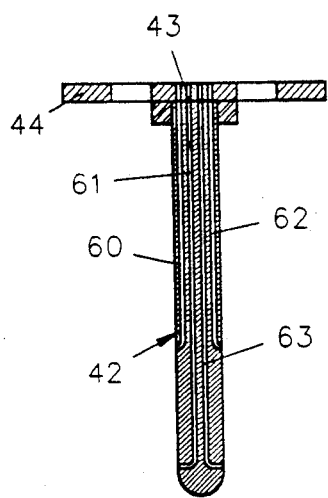
FIG. 4 is a longitudinal cross-sectioned view of the post member used in the instrument of the present invention.

The fingers 52 and 53 are formed of a resilient material and have an arcuate curvature when in the relieved condition. It will be seen that the angular positions of the fingers 52 and 53 in the openings 46 and 47 determines the directions in which the fingers spread out with respect to one another and to the central post 42. A plurality of filaments 55, 56, 57, and 58 are connected at the distal ends thereof by means of a plurality of swivel connectors 59 to the fingers 52 and 53 as shown in FIG. 3, and extend through passageways 60, 61, 62, and 63 in the post 42 and the flange 44 as also shown in FIG. 4. The passageways extend from the sides of the post facing the fingers 52 and 53 to the outer face of the flange 44 from which the filaments 55, 56, 57, and 58 extend for manipulation of the fingers 52 and 53 by the surgeon or other person.

The spring fingers 52 and 53 are each provided with a plurality of longitudinally spaced serrated sections 52B and 52C and 53B and 53C which are used in combination with a clamp 60 to lock the fingers 52 and 53 in the longitudinally adjusted positions.

Figure 5:
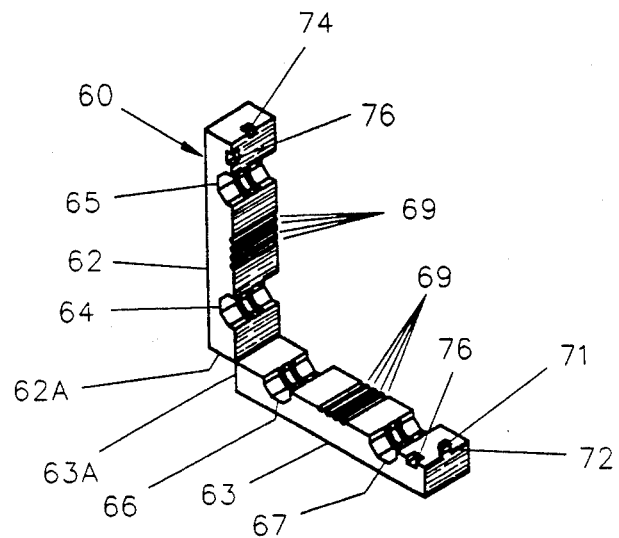
FIG. 5 is an isometric view of the clamp member used in the instrument of the present invention.
Figure 6:
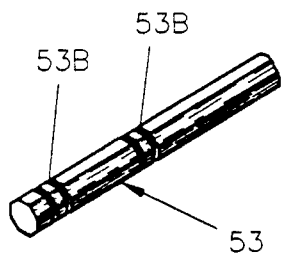
FIG. 6 is an end view of one of the fingers used in the instrument of the present invention.
Figure 7:
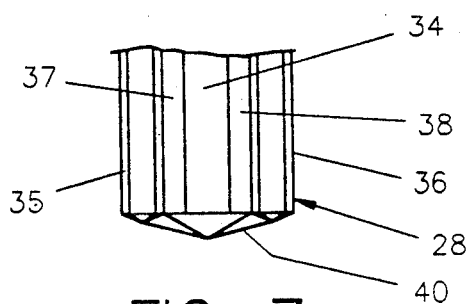
FIG. 7 is a fragmentary elevational view of the incisor part of the instrument of the invention particularly showing the cutting end of an incision tool.
Figure 8:
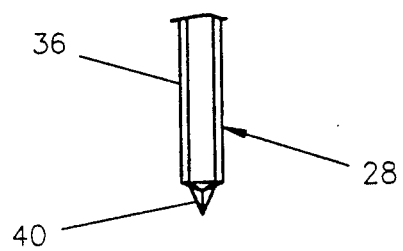
FIG. 8 is a fragmentary side view of the incisor part shown in FIG. 7.

The clamp 60 consists of a pair of rigid members 62 and 63 which are hingedly connected together at the respective ends 62A and 63A thereof. The members 62 and 63 are provided with transverse grooves 64, 65, 66, and 67 which are sized and serrated to receive and grasp the serrated sections of the fingers 52 and 53 to prevent inward movement of the fingers relative to the clamp 60 and the flange 44. A plurality of slots 69 are provided in the members 62 and 63 for slidably receiving the filaments 55, 56, 57, and 58 when the clamp is closed. A latching finger 71 having an undercut 72 extends upwardly from the clamp member 63 as shown in FIG. 5 for interlocking engagement with the clamp member 62 in a complementary opening 74 therein. The members 62 and 63 are preferably formed of plastic and are sufficiently resilient to permit the finger 71 to be snapped in and out of the opening 74. A pair of narrow slots 76 are provided in the clamp members 62 and 63 for receiving the handle of a scalpel or other tool for prying the clamp members away from one another to release the fingers 52 and 53 and the filaments 55, 56, 57, and 58.

In use the incision tool 12 is initially inserted into the introducer 10, and after a skin incision has been made, the introducer and the incision tool 12 are then pressed as a unit against the underlying tissues of the patient at the location where the retractor tool is to be inserted into the body of the patient thereby to fully insert the introducer into the body of the patient. Introducers and incision tools having different lengths are provided so that the end of the selected pair extends only a short distance beyond the inner boundary of the body wall into the body cavity. If desired, the blade 40 may be shrouded by a spring-loaded retractable shroud to prevent damage to the internal organs of the body as the incision tool and the introducer are pushed through the body wall into the body cavity. Then, with the introducer in place, the incision tool 12 is retracted from the introducer and replaced by the organ retractor tool 14. The post, the fingers and the bridging filaments can be maneuvered within the body cavity to push the organs within the body cavity to a desired location and then to hold them in such location. Upon completion of the surgery, the clamp 60 is released and the filaments ar pulled outwardly to straighten the distal end portions of the fingers so that they can be easily withdrawn from the body cavity through the introducer or the introducer and the retractor tool can be withdrawn as a unit from the patient.

An important feature of the present invention is the fact that the surgeon can adjust the directions in which the fingers spread out with respect to one another and to the center post 42. These directions can be initially set by rotating the fingers in the respective openings 46 and 47. If during the surgery it becomes desirable to readjust the directions in which the fingers spread out, the retractor tool can be partially withdrawn from the introducer and the fingers can then be pushed clear of the flange 44 and rotated to the desired position before reinsert them into the openings 46 and 47.

While the present invention has been disclosed in connection with a particular embodiment thereof, it will be understood that many changes and modifications can be made therein without departing from the true spirit and scope of the invention. Therefore, it is intended by the appended claims to cover all such changes and modifications that come within the true spirit and scope of the invention.

I claim:

1. An organ retractor, comprising in combination tubular introducer means for insertion through a body wall into an underlying body cavity,
organ retractor means slidably movable through said introducer,
said organ retractor means including a rigid post, at least one flexible pre-biased, spring finger mounted adjacent said rigid post, and one or more filaments connected between said finger and said post.

2. An organ retractor according to claim 1,
said post and said one or more fingers having rounded distal ends.

3. An organ retractor according to claim 2, comprising
a first flange at the exterior end of said introducer, and
a second flange at the exterior end of said post.

4. An organ retractor according to claim 3, comprising seal means adapted to be compressed in sealing relationship between said flanges when said post is fully inserted into said introducer.

5. An organ retractor, comprising in combination tubular introducer means for insertion through a body wall into an underlying body cavity, organ retractor means slidably movable through said introducer, said organ retractor means including at least one flexible, spring finger, a rigid post, and one or more filaments connected between said finger and said post, and swivel means connecting said one or more filaments to said finger.

6. An organ retractor according to claim 5 wherein said organ retractor tool comprises two flexible pre-biased fingers respectively located on opposite sides of said post.

7. An organ retractor, comprising in combination tubular introducer means for insertion through a body wall into an underlying body cavity, organ retractor means slidably movable through said introducer, said organ retractor means including at least one flexible, spring finger, a rigid post, and one or more filaments connected between said finger and said post, and said one or more filaments extend through one or more longitudinal passageways in said post and are manually accessible at the end of said retractor tool disposed externally of said body wall.

8. An organ retractor according to claim 7, comprising a flange means affixed to one end of said post, said flange having a polygonal opening therethrough for slidably receiving said finger, said finger having a cross-sectional shape complementing the shape of said opening.

9. An organ retractor according to claim 8, comprising clamp means for clamping said filaments and said fingers in the adjusted positions.

10. An organ retractor according to claim 9, said post having a plurality of longitudinal passageways respectively receiving said filaments.

* * * * *